US005765549A

United States Patent [19]

Kolbe et al.

[11] Patent Number: 5,765,549

[45] Date of Patent: Jun. 16, 1998

[54] RESPIRATOR

[75] Inventors: Günther Kolbe, Mölln; Wolfgang Drews, Zarpen; Werner Jumpertz, Stockelsdorf, all of Germany

[73] Assignee: Drägerwerk AG, Lübeck, Germany

[21] Appl. No.: 858,624

[22] Filed: May 20, 1997

[51] Int. Cl.[6] .......... A61M 15/00

[52] U.S. Cl. .......... 128/202.26; 128/205.12; 128/205.22

[58] Field of Search .......... 128/202.26, 205.12, 128/205.22

[56] References Cited

U.S. PATENT DOCUMENTS

| | | | |
|---|---|---|---|
| 2,456,130 | 12/1948 | Lambertsen | 128/205.12 |
| 2,483,116 | 9/1949 | Yarbrough | 128/205.12 |
| 4,140,765 | 2/1979 | Martin et al. | 128/202.26 |
| 4,154,234 | 5/1979 | Baker | 128/205.12 |
| 4,164,218 | 8/1979 | Martin | 128/202.26 |
| 4,233,971 | 11/1980 | Gronau et al. | 128/205.12 |
| 4,840,170 | 6/1989 | Dahrendorf et al. | 128/202.26 |
| 5,113,854 | 5/1992 | Dosch et al. | 128/205.22 |
| 5,203,325 | 4/1993 | Carr | 128/202.26 |
| 5,222,479 | 6/1993 | Brauer et al. | 128/205.12 |
| 5,267,558 | 12/1993 | Haertle et al. | 128/205.12 |

FOREIGN PATENT DOCUMENTS 33 24 222 C2 7/1984 Germany .

*Primary Examiner*—Aaron J. Lewis
*Attorney, Agent, or Firm*—McGlew and Tuttle

[57] ABSTRACT

A respirator to be worn in front of the chest with regeneration of the breathing air, containing a regenerating cartridge with a plurality of chemical layers, a breathing bag, a connection piece on the side of the breathing bag located opposite the regenerating cartridge, a breathing hose pointing from the connection piece to the user, and an oxygen-releasing starting device at the regenerating cartridge. The supply of oxygen into the breathing bag and the wear properties are improved by the breathing bag being designed as a bag lying flat on the regenerating cartridge and having a ring-shaped hose part, which can be laid around the neck of the user. This provides a neck opening formed within the breathing bag. An opening is provided in the chemical layer located opposite the breathing bag. A starting device is accommodated in this opening such that it is in flow connection with a collector chamber opening into the breathing bag.

8 Claims, 2 Drawing Sheets

RESPIRATOR

FIELD OF THE INVENTION

The present invention pertains to a respirator with a regenerating cartridge with a breathing in pipe branch, which extends through a first chemical layer and is connected to a disk-shaped distribution chamber, the distribution chamber being in contact with a first chemical layer at one side and being in contact with a second chemical layer at another side and with a collector chamber which is connected to a breathing-out opening and extends at least over a section, at a wall of the regenerating cartridge, and accommodates even gas flow arriving from the distribution chamber through the chemical layers, a breathing bag connecting to the breathing out opening and an oxygen-releasing starting device.

BACKGROUND OF THE INVENTION

A respirator of this type with a regenerating cartridge, which binds carbon dioxide and releases oxygen at the same time, has become known from DE-PS 33 24 222. Good mixing of the breathing gas to be regenerated and good utilization of the chemicals are achieved in the prior-art respirator due to the uniform distribution of the gas flows within the regenerating cartridge among the chemical layers. However, the oxygen supply for the user is unsatisfactory immediately after the respirator is put into operation, because the oxygen generated by the starting device reaches the breathing bag only after flowing through purifying layers. In addition, the starting device is fastened at an exposed point on the top side of the regenerating cartridge in the area of the breathing bag, so that the respirator cannot be folded up in a space-saving manner. In addition, there is a risk that the breathing bag may be damaged by the heat generated within the starting device during the chemical reaction. Furthermore, separate strapping is necessary to fasten the respirator on the neck of a user.

SUMMARY AND OBJECTS OF THE INVENTION

The primary object of the present invention is to improve a respirator of this type with respect to oxygen supply into the breathing bag and the wear properties.

This object is accomplished by the breathing bag being designed as a bag lying flat on the regenerating cartridge and having a ring-shaped hose part which can be laid around the user's neck and by which a neck opening is formed within the breathing bag; by the second chemical layer being provided with a first opening, in which the starting device is accommodated such that it is in flow connection with the collector chamber opening into the breathing bag.

The advantage of the present invention is essentially that a space-saving integration of the starting device within the housing of the regenerating cartridge and a direct feed of oxygen into the breathing bag is made possible due to the starting device being arranged within an opening of the second chemical layer, which is in connection with the collector chamber receiving the purified breathing air. The underside of the cartridge housing may be provided with a coating having poor thermal conductivity for thermal insulation of the starting device against the environment. The respirator according to the present invention can be put on in an especially simple manner by means of the hose part, which is connected to the breathing bag and is laid around the user's neck, and it also has good wear properties.

The hose part is advantageously designed as part of the volume of the breathing bag. The volume of the breathing bag can thus be effectively enlarged, so that the total amount of oxygen generated by the starting device can be stored. The enlarged breathing bag also prolongs the use time of the respirator, because the oxygen can be consumed even when the oxygen production in the chemical has ceased, but the binding of carbon dioxide is still possible.

The breathing bag is preferably dimensioned to have a total volume greater than 6 liters. This volume can be obtained by using the ring portion as part of the volume of the bag.

The second open space present at the regenerating cartridge in the area of the breathing-in pipe branch is dimensioned such that the connection piece can be inserted into it.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
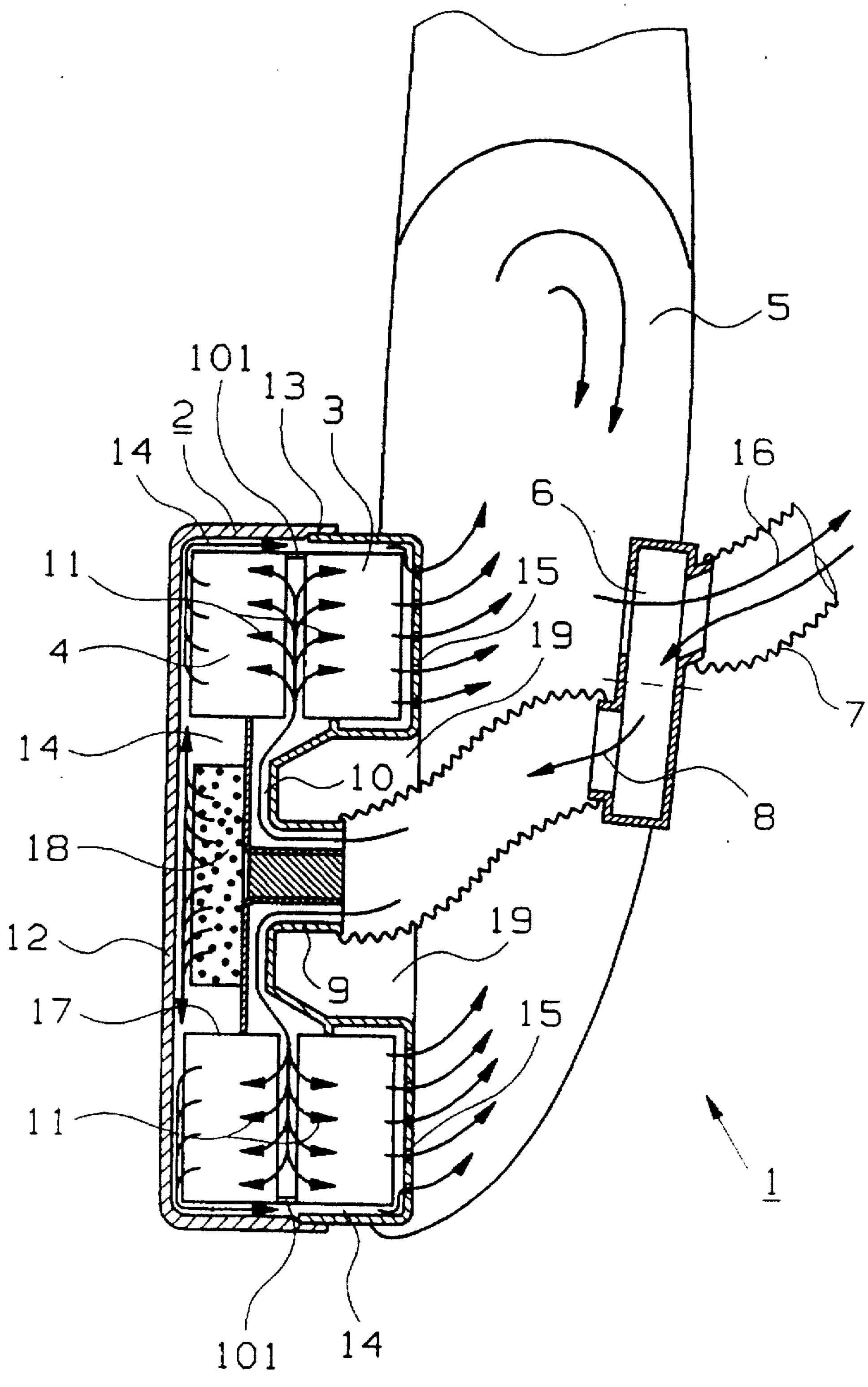
FIG. 1 is a longitudinal sectional view of the respirator.
Figure 2:
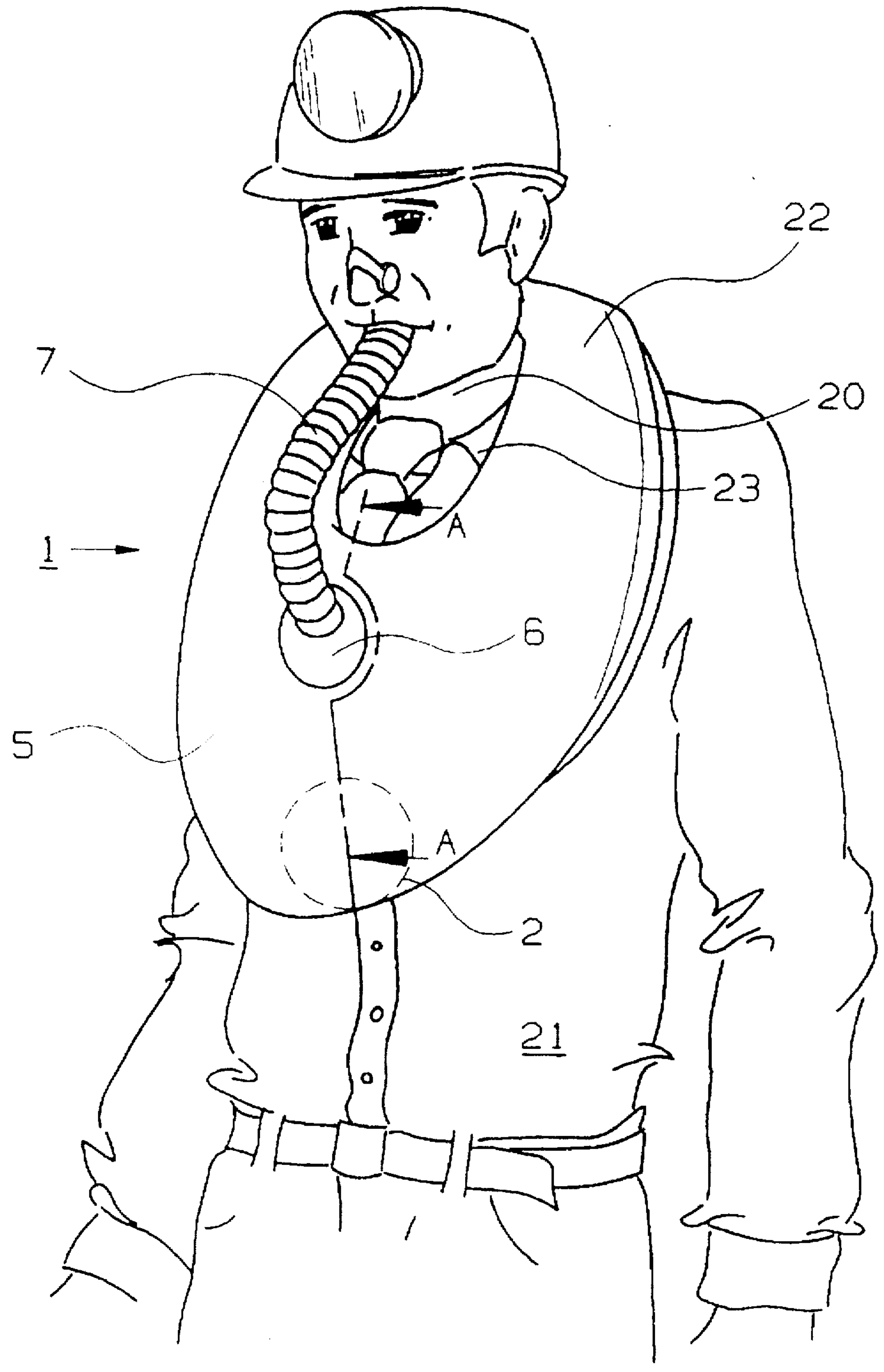
FIG. 2 is a perspective view showing the respirator according to FIG. 1 in the position of use.

FIG. 1 shows schematically the longitudinal section of a respirator 1 along section line A—A in FIG. 2. The respirator 1 comprises a regenerating cartridge 2 with an oxygen-generating and carbon dioxide-binding, first chemical layer 3, a second chemical layer 4, a breathing bag 5, a connection piece 6 with a heat exchanger, not shown in FIG. 1, and a breathing tube 7, which is connected to the connection piece 6 and leads to a user, not shown in FIG. 1. The chemical layers 3, 4 preferably consist of potassium peroxide. The gas exhaled by the user enters a inhaled air flange 9 of the regenerating cartridge 2 along a first flow path 8 and from there via a disk-shaped distribution chamber 10, with which the ring-shaped chemical layers 3, 4 are in contact. The breathing gas flow is split axially via the cross-sectional surfaces of the disk-shaped chemical layers 3, 4 along the arrows 11 within the distribution chamber 10. A collector chamber 14 extends on the bottom part 12 and at the side walls 13 within the regenerating cartridge 2, and the said collector chamber 14 receives the gas which leaves the chemical layers 3, 4, is purified of carbon dioxide and is enriched with oxygen, and releases it into the breathing bag 5 via a breathing-out opening 15. The user can take oxygen from the breathing bag 5 along a second flow path 16. Direct overflow of breathing gas from the distribution chamber 10 into the collector chamber 14 is prevented by partitions 101 between the distribution chamber 10 and the collector chamber 14. A starting device 18, which releases oxygen directly into the collector chamber 14 and to the exhaled air outlet 15 via the side walls 13, is arranged in a first open space 17 within the second chemical layer 4 on the bottom part of the regenerating cartridge 2. Thus, the oxygen is available to the user immediately after the ignition of the starting device 18. A second open space or recess 19 is dimensioned such that the connection piece 6 can be inserted, is provided in the housing of the regenerating cartridge 2 between the exhaled air outlet 15 and the inhaled air flange 9. The respirator 1 can thus be folded up in an especially space-saving manner.

FIG. 2 shows the respirator 1 according to FIG. 1 in the ready-to-use state. To fasten the respirator I on the neck 20 of a user 21, the breathing bag 5 is provided with a hose part 22, by which a circular neck cutout 23 is formed. The hose part 22 is an integral part of the breathing bag 5. On the one hand, the volume of the breathing bag 5 is increased by the hose part 22 to a value of about 6 L, and, on the other hand, the need for a strap for fastening the regenerating cartridge 2 is eliminated, because the regenerating cartridge is held directly by the breathing bag 5. The regenerating cartridge 2 is covered by the breathing bag 5 in FIG. 2, and it lies directly on the chest of the user 21. The total amount of oxygen generated can be used for breathing due to the size of the breathing bag 5, because the total amount of oxygen generated in a relatively short time can be stored in the breathing bag 5, especially during the starting phase, after the activation of the starting device 18. After the chemical layers 3, 4 have been consumed, the oxygen still present in the breathing bag 5 can be completely exhausted, because the binding of carbon dioxide in the chemical layers 3, 4 is still possible even when the oxygen production is already exhausted.

While a specific embodiment of the invention has been shown and described in detail to illustrate the application of the principles of the invention, it will be understood that the invention may be embodied otherwise without departing from such principles.

What is claimed is:

1. A respirator with regeneration of the breathing air, comprising:

a regenerating cartridge with a inhaled air flange and a exhaled air outlet and an outer wall;

a disk-shaped distribution chamber;

a first chemical layer, inhaled air flange extends through said first chemical layer and is connected to a said disk-shaped distribution chamber, said first chemical layer being in contact with one side of said disk-shaped distribution chamber;

a second chemical layer in contact with another side of said distribution chamber;

a collector chamber connected to said exhaled air outlet and extending at least over a section at said outer wall of said regenerating cartridge, said collector chamber accommodating gas flow arriving from said distribution chamber through said first chemical layer and said second chemical layer;

a breathing bag with an interior space, said breathing bag being connected to said exhaled air outlet, said breathing bag being configurable to lye flat on said regenerating cartridge and having a ring-shaped part which can be laid around a neck of a user and which defines a neck opening formed within said breathing bag to position said regenerating cartridge in front of a user's chest;

a connection piece on a side of said breathing bag located opposite said regenerating cartridge, said connection piece being connected to said inhaled air flange via a first flow path and being connected to said interior space of said breathing bag via a said second flow path and having a breathing hose directed toward a user; an oxygen-releasing starting device at said respirator, said second chemical layer being provided with a first opening, in which said starting device is accommodated such that said starting device is in flow connection at least with said collector chamber.

2. A respirator in accordance with claim 1, wherein said ring shaped part includes a hose part defining a portion of the volume of said breathing bag.

3. A respirator in accordance with claim 1, wherein said breathing bag has a volume larger than 6 L.

4. A respirator in accordance with claim 1 wherein said regenerating cartridge has a recess in an area of said inhaled air flange, said recess being dimensioned such that said connection piece can be inserted into it.

5. A respirator with regeneration of the breathing air, comprising:

a regenerating cartridge with a inhaled air flange and a exhaled air outlet;

a disk-shaped distribution chamber;

a chemical layer, inhaled air flange extends through said chemical layer and is connected to a said disk-shaped distribution chamber, said chemical layer being in contact with a side of said disk-shaped distribution chamber;

another chemical layer in contact with another side of said distribution chamber;

a collector chamber connected to said exhaled air outlet and extending at least over a section of said regenerating cartridge, said collector chamber accommodating gas flow arriving from said distribution chamber through said chemical layer and said another chemical layer;

a breathing bag with an interior space, said breathing bag being connected to said exhaled air outlet, said breathing bag being configurable to lye flat on said regenerating cartridge and having a ring-shaped part which can be laid around a neck of a user and which defines a neck opening formed within said breathing bag to position said regenerating cartridge in front of a user's chest;

a connection piece on a side of said breathing bag located opposite said regenerating cartridge, said connection piece being connected to said inhaled air flange via a first flow path and being connected to said interior space of said breathing bag via a said second flow path and having a breathing hose;

an oxygen-releasing starting device at said respirator, said second chemical layer being provided with a first opening, in which said starting device is accommodated such that said starting device is in flow connection at least with said collector chamber.

6. A respirator in accordance with claim 5, wherein said ring shaped part includes a hose part defining a portion of the volume of said breathing bag.

7. A respirator in accordance with claim 5, wherein said breathing bag has a volume larger than 6 L.

8. A respirator in accordance with claim 5 wherein said regenerating cartridge has a recess in an area of said inhaled air flange, said recess being dimensioned such that said connection piece can be inserted into it.

* * * * *